(12) United States Patent
Annis

(10) Patent No.: US 7,221,732 B1
(45) Date of Patent: May 22, 2007

(54) METHOD AND APPARATUS FOR PRODUCING LAMINOGRAPHY IMAGES USING A FIXED X-RAY SOURCE

(76) Inventor: Martin Annis, 67 Banks St., Cambridge, MA (US) 02138

( * ) Notice: Subject to any disclaimer, the term of this patent is extended or adjusted under 35 U.S.C. 154(b) by 0 days.

(21) Appl. No.: 11/394,406

(22) Filed: Mar. 31, 2006

Related U.S. Application Data (60) Provisional application No. 60/696,646, filed on Jul. 5, 2005, provisional application No. 60/668,412, filed on Apr. 4, 2005.

(51) Int. Cl.
*G01N 23/04* (2006.01)
*H05G 1/64* (2006.01)
*H05G 1/00* (2006.01)

(52) U.S. Cl. .................... 378/57; 378/98.8; 378/14; 378/9

(58) Field of Classification Search .............. 378/9, 378/10, 21, 26, 54, 57, 62, 86, 88, 146, 19, 378/98.8, 14, 58; 250/358.1, 359.1, 360.1
See application file for complete search history.

(56) References Cited

U.S. PATENT DOCUMENTS

| | | | | |
|---|---|---|---|---|
| 4,956,856 | A * | 9/1990 | Harding | 378/88 |
| 5,007,072 | A * | 4/1991 | Jenkins et al. | 378/88 |
| 5,428,657 | A * | 6/1995 | Papanicolopoulos et al. | 378/86 |
| 6,018,562 | A * | 1/2000 | Willson | 378/9 |
| 6,122,344 | A * | 9/2000 | Beevor | 378/88 |
| 6,628,745 | B1 * | 9/2003 | Annis et al. | 378/21 |
| 7,020,241 | B2 * | 3/2006 | Beneke et al. | 378/57 |
| 2003/0231739 | A1 * | 12/2003 | Rosner | 378/57 |

\* cited by examiner

*Primary Examiner*—Edward J. Glick
*Assistant Examiner*—Irakli Kiknadze (57) ABSTRACT

An imaging system and method for taking an image of an object. The imaging system comprises a mechanism that propels the object linearly in a direction of motion through an imaging region that has a top, bottom, front, and rear; an x-ray source located below the bottom, aligned with the front, and emitting an x-ray cone beam to the imaging region; and a plurality of x-ray detector assemblies, each of the detector assemblies including a linear row of detectors above and parallel to the top and perpendicular to the direction of motion, and a linear column of detectors outside of and parallel to the rear right side and extending at an angle to the direction of motion, wherein each of the detector assemblies defines an x-ray fan beam within the x-ray cone beam. A second system embodiment duplicates the x-ray source/detector assemblage and rotates the second assemblage by 90° around the object. In the method, a number of x-ray fan beams are emitted from a single location at different angles and the object is propelled linearly through the fan beams. The x-ray intensity of each fan beam passing through a voxel is read and those x-ray intensities are combined in accordance to standard laminography practice to generate an image for the voxel. In this way, images for all voxels are generated and used to produce an image of the entire object. With the second system embodiment, two sets of voxel images are generated, which allows views from a full 180° for all voxels in the object. Applying computer tomography reconstruction algorithms can produce CT images.

12 Claims, 6 Drawing Sheets

METHOD AND APPARATUS FOR PRODUCING LAMINOGRAPHY IMAGES USING A FIXED X-RAY SOURCE

CROSS-REFERENCES TO RELATED APPLICATIONS

The applicant wishes to claim the benefit of U.S. Provisional Patent Application No. 60/668,412, filed Apr. 4, 2005 for LAMINOGRAPHY WITH FIXED X-RAY SOURCE in the name of Martin Annis, and U.S. Provisional Patent Application No. 60/696,646, filed Jul. 5, 2005 for LAMINOGRAPHY WITH TWO FIXED X-RAY SOURCES in the name of Martin Annis.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to laminography, more particularly, to a method for creating laminography images without the need for a moving x-ray source.

2. Description of the Related Art

One of the digital laminography systems invented by the current inventor uses an x-ray source that moves laterally and rapidly across the object while the object moves more slowly longitudinally (i.e., perpendicular to the lateral motion). Blurring of the pixels that are not focused is accomplished by selecting x-rays that are detected by a line of detectors in the lateral plane at the appropriate times. Recently, this procedure was improved by employing multiple lines of detectors that allow blurring in two dimensions, the lateral one and a longitudinal one.

BRIEF SUMMARY OF THE INVENTION

An object of the present invention is to provide a laminography system that employs a fixed x-ray source to simplify the design and reduce the cost.

The present invention is an apparatus and method that uses one or two fixed x-ray source(s) to produce laminography images. The object moves on a conveyor belt in a longitudinal direction of motion through an imaging area. A conventional x-ray source emits a cone beam into the imaging area from a location below and to the left of the imaging region. A plurality of x-ray detector assemblies are located outside the imaging region opposite the x-ray source. Each L-shaped detector assembly has a detector row above the top of the imaging region and a detector column outside the rear wall. Each of the detector assemblies 16 defines an x-ray fan beam within the imaging region. Optional slit collimators cooperate with the detector assemblies to better define the fan beams and to reduce cross-talk.

The central fan beam is in the vertical plane, perpendicular to the object's direction of motion. The other fan beams define planes at various angles $\phi$ to the vertical fan beam. The range of angles $\phi$ may be as great as $-45°$ to $+45°$. The detectors are spaced so that they line up in the direction of motion with the corresponding detectors in the central detector assembly. This means that the detector rows are identical. For the side detectors, since the detector columns are not parallel, the detector column detectors are spaced apart proportionally to $1/\cos \phi$.

The second embodiment of the present invention is essentially two copies of the assemblage of the x-ray source/collimators/detector assemblies assemblage of the first embodiment rotated 90° apart.

Every voxel falls in one of two regions of the imaging region, where the regions are defined by a dividing line that runs between the x-ray source and the uppermost detector of the detector column. To focus a voxel in the front region, the detector rows are used, and to focus a voxel in the rear region, the detector columns are used.

The method of the present invention starts by emitting a number of x-ray fan beams from a single location at different angles and the object is propelled linearly through the fan beams. The x-ray intensity of that portion of a fan beam passing through a voxel is read for all of the fan beams and those x-ray intensities are combined in accordance to standard laminography practice to generate an image for the voxel. This is performed for all voxels of the object and the resultant voxel images are used to produce an image of the entire object.

For the embodiments of the present invention, in order to focus a voxel, a detector in each fan beam that lines up with the voxel as it passes through the fan beam is sampled and the x-ray intensities from those detectors are summed. This entails first determining the distance x that the voxel travels from one fan beam to the next and the time T that it takes to do so. This is determined by the equation $x=(z*\tan(\phi_a))/V$, where z is the vertical distance from the x-ray source to the voxel, $\phi_a$ is the angle of the fan beam, and V is the speed of the object. For voxels in the front region, the location of the particular detector, $L_j$, in the detector row to sample for the voxel is determined by the equation $L_j = y_{j,0} * L_H / z_{j,0}$, where $y_{j,0}$ is the horizontal distance in the y direction of the voxel from the x-ray source, $L_H$ is the vertical distance from the x-ray source to the detector row, and $z_{j,0}$ is the vertical distance from the x-ray source to the voxel. For voxels in the rear region, the equivalent detector location equation is $L_{k,a} = (L_W * z_{k,0}) / (y_{k,0} * \cos(\phi_a))$, where $y_{k,0}$ is the horizontal distance in the y direction of the voxel from the x-ray source. The sample signal from each fan beam for the voxel is used to obtain the laminography blurred sum.

The process is repeated for all of voxels of the object to produce laminography images in xz planes.

The same algorithm is employed with each assemblage of the second embodiment. The resultant "views" of the second assemblage are different from the first. The additional assemblage allows views from a full 180° for all voxels in the object. Thus, computed tomography (CT) reconstruction algorithms can be used to produce CT imaging.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

The present invention is an apparatus and method that uses one or two fixed, i.e., not moving, x-ray source(s) to produce laminography images as the object to be imaged moves longitudinally across the x-ray source. The invention can also be applied as the x-ray source(s) move longitudinally across a stationary object. In both configurations, since the rapid lateral motion of the x-ray source of the prior art is not required, conventional x-ray sources can be used to produce laminography images in the same amount of time as in the methods of the prior art. The present invention became practical with the improvement of the small detectors used in digital imaging and the lowering in cost of each detector.

Figure 1:
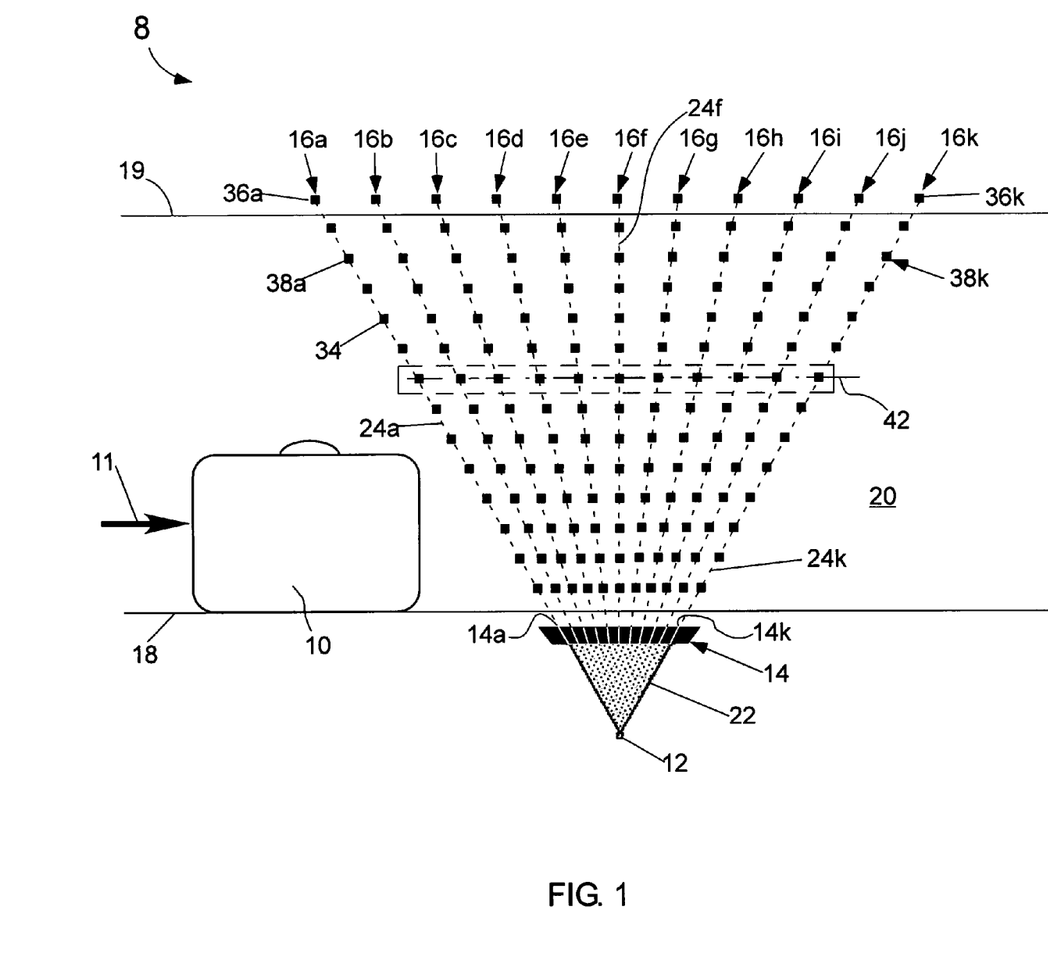
FIG. 1 is a side view of a device of the single x-ray source apparatus of the present invention.
Figure 2:
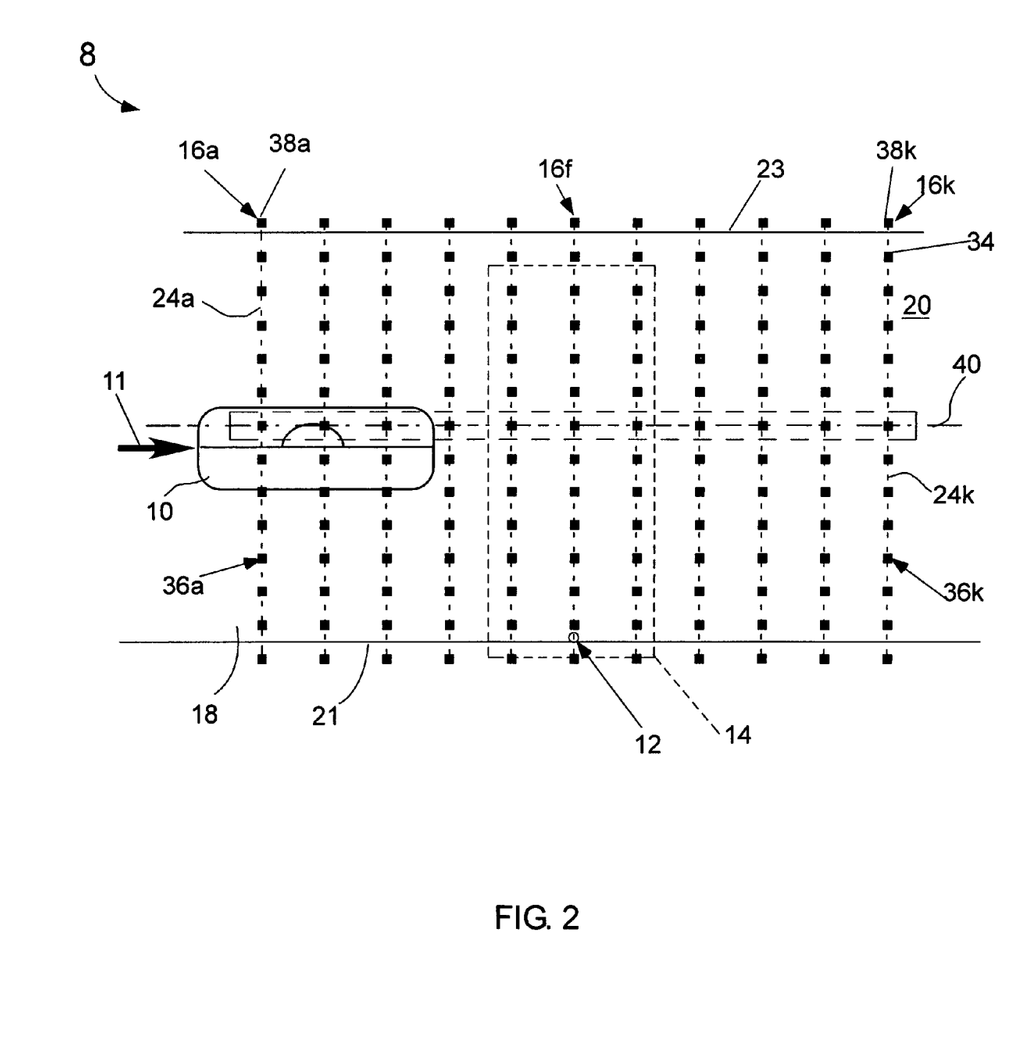
FIG. 2 is a top view of the device of FIG. 1.
Figure 3:
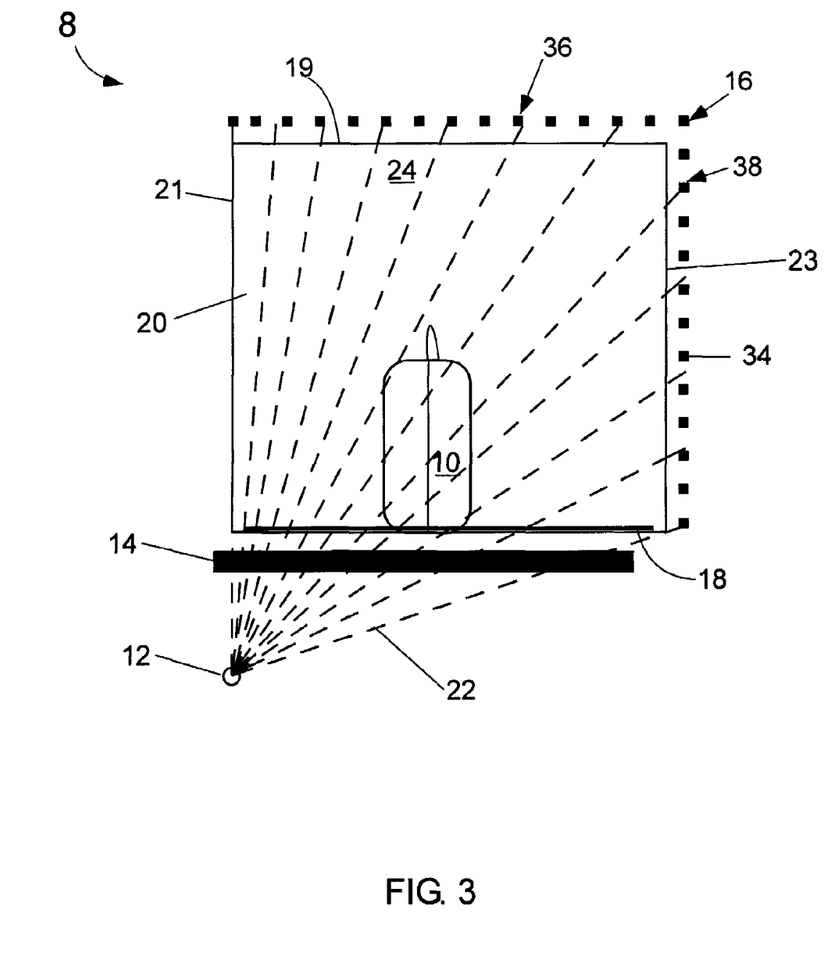
FIG. 3 is an end view of the device of FIG. 1.
Figure 4:
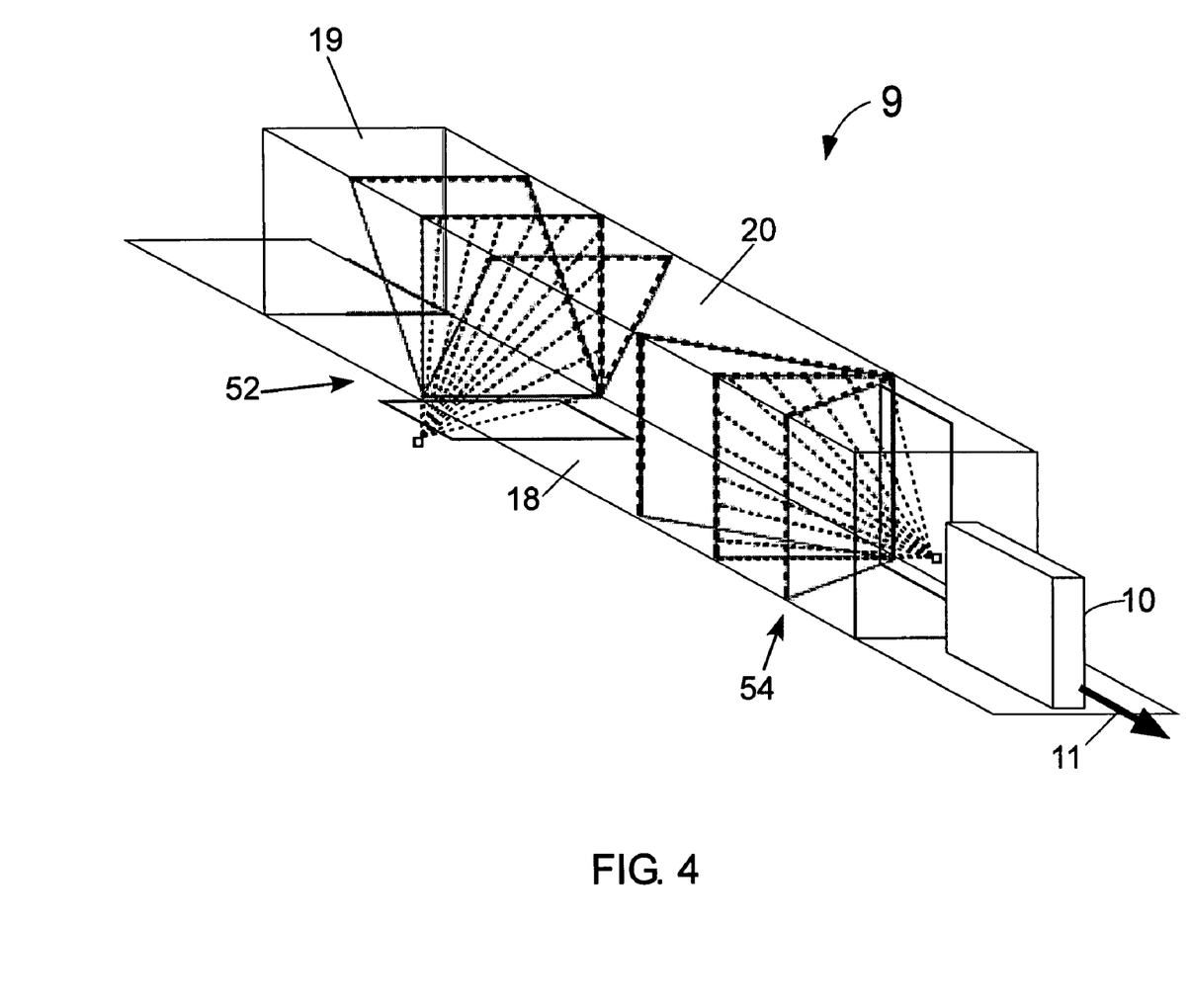
FIG. 4 is a perspective view of a device of the two x-ray source apparatus of the present invention.

There are two embodiments of the present invention. The first embodiment 8 employs a single x-ray source and is shown in FIGS. 1-3. The second embodiment 9 employs two x-ray sources and is shown in FIG. 4. The illustrated configurations for both embodiments have the x-ray source and x-ray detectors fixed with the object in motion. As indicated above, the present invention contemplates that the object can be stationary with the x-ray source and detectors in motion.

In the first embodiment 8, illustrated in FIGS. 1-3, the object 10 moves on a conveyor belt 18 in a longitudinal direction of motion 11. Generally, the conveyor belt 18 is enclosed in a tunnel in order to reduce x-ray exposure for protective purposes. The area within the tunnel that the object 10 passes through is the imaging region 20. The imaging region 20 is generally a rectangular parallelepiped (a three-dimensional rectangle). The present specification and claims refer to the bottom, top, front, and rear of the imaging region 20. This is merely a convenience and is not intended as an absolute positional requirement. The present invention contemplates that the absolute positions of the various components may be different than as discussed, as long as the relative positions of the various components remain the same.

The x-ray source 12 is a conventional one that emits a cone beam 22. As can be seen in FIG. 3, the x-ray source 12 is located relative to the imaging region 20 such that the entire cross-sectional area of the imaging region 20 is within the cone beam 22 without any corner cut-off. In the example of FIG. 3, the x-ray source 12 is located below the conveyor belt 18 (under the bottom of the imaging region 20) and is generally aligned with or outside of the front wall 21 of the imaging region 20. The typical maximum energy of the x-ray source 12 may be between 100 keV and 400 keV. The maximum energy may be as great as 2.5 MeV if single fan beams (described below) illuminate the entire imaging region cross-section. The example below is for an energy of about 150 keV, suitable for the inspection of airport luggage.

A plurality of x-ray detector assemblies 16a-16k (collectively, 16) are located outside the imaging region 20 opposite the x-ray source 12. Each L-shaped detector assembly 16 is comprised of a number of detectors 34 arranged in a detector row 36a-36k (collectively, 36) above the top 19 of the imaging region 20 and a detector column 38a-38k (collectively, 38) outside the rear wall 23. Each of the detector assemblies 16 defines an x-ray fan beam 24a-24k (collectively, 24). In the example of the figures, there are eleven fan beams 24a-k, a number that is used throughout the present specification. This number is only intended as an example. The preferred number of detector assemblies 16 is greater than ten and the number can range as high as necessary to achieve a desired number of focused planes within the object 10.

Optionally, a number of slit collimators 14a-14k (collectively, 14) are placed between the x-ray source 12 and the imaging region 20. The collimators 14 cooperate with the detector assemblies 16 to better define the fan beams 24. Although not strictly necessary, the collimators 14 are desirable in order to reduce crosstalk between fan beams 24 to obtain better images.

The central fan beam 24f is in the vertical plane, perpendicular to the direction of motion 11 of the object 10 being imaged. The other fan beams 24a-e,g-k, however, define planes at various angles φ to the vertical fan beam 24f. The range for φ depends upon the particular application, and may be as great as −45° to +45°. In other words, fan beam 24a may be up to −45° from vertical and fan beam 24k may be up to +45° from vertical. The remainder of the fan beams are generally evenly distributed therebetween. Each fan beam is denoted by an index, a, where the central fan beam is a=0. The angle of the a'th fan beam is $\phi_a$. In the figures, there are eleven fan beams 24, so a=−5, −4, −3, −2−, 1, 0, +1, +2, +3, +4, +5.

As a consequence of the detector arrangement of the present invention, the blurring of the intervening regions is different from a prior art system that uses a rapidly moving x-ray fan beam in one plane. This means that a long horizontal object below or above the desired voxel to be focused and parallel to the central row of detectors will be avoided in many of the detectors. On the other hand, an object 10 that is relatively long in the direction of motion 11 of the object 10 will be difficult to blur because all of the x-rays in the same y plane penetrate this long, object no matter how high it is in the yz plane, and therefore this long object is not blurred. This latter effect can be avoided by tilting either the axis of the x-ray source 12 or the object 10 so that the plane of the central fan beam 24f is not perpendicular to the direction of motion 11 of the long object 10. This will avoid a problem with the confusion caused by the sides, front, and back of a cargo container, for example.

Theoretically, each detector assembly 16 has the same number of detectors 34 and the detectors 34 are spaced so that they line up longitudinally (direction of object motion 11) with the corresponding detectors 34 in the central detector assembly 16f, as at 40, 42. For the top detector lines 40 of the detector rows 36, this simply means that the detector rows 36 are identical, as can be seen in FIG. 2. However, as can be seen in FIG. 1, for the side detector lines 42 of the detector columns 38, since the detector columns 38 are not parallel, the detectors 34 of these detector columns 38a-e,g-k must be spaced apart proportionally to 1/cos $\phi_a$ in order to maintain the detectors 34 in the side detector lines 42.

The second embodiment 9 of the present invention is shown in FIG. 4. This embodiment 9 is essentially two copies of the assemblage of the x-ray source 12, collimators 14, detector assemblies 16 rotated 90° apart. FIG. 4 illustrates one contemplated configuration of the two assemblages 52, 54. The first assemblage 52 is located at one end of the imaging region 20 and the second assemblage 54 is located at the other end of the imaging region 20. Other configurations that provide the same functionality are contemplated.

Optionally, each detector 34 in each of the detector assemblies 16 is sampled twice as the shadow of the focused voxel passes over the detector 34. Each of these two samples provides an independent spatial row of data separated by one half of the longer detector dimension in the longitudinal direction 11, in accordance with the Nyquist theorem. The width of the fan beam 24 as defined by the slit collimator 14 overfills the detectors 34, so the fan beam 24 is moving across the focused voxel in the longitudinal direction 11. Thus, the detectors 34 have twice the longitudinal dimension as the perpendicular dimension, since the Nyquist theorem does not apply in the perpendicular dimension. This sampling is done typically every few milliseconds to produce about 1000 longitudinal sets of data in a few seconds. This compares to the necessity in one of the related prior art systems that each detector be sampled every few microseconds. Thus, the detectors 34 do not have to have the same quality as in one of the systems of the related art.

Figure 5:
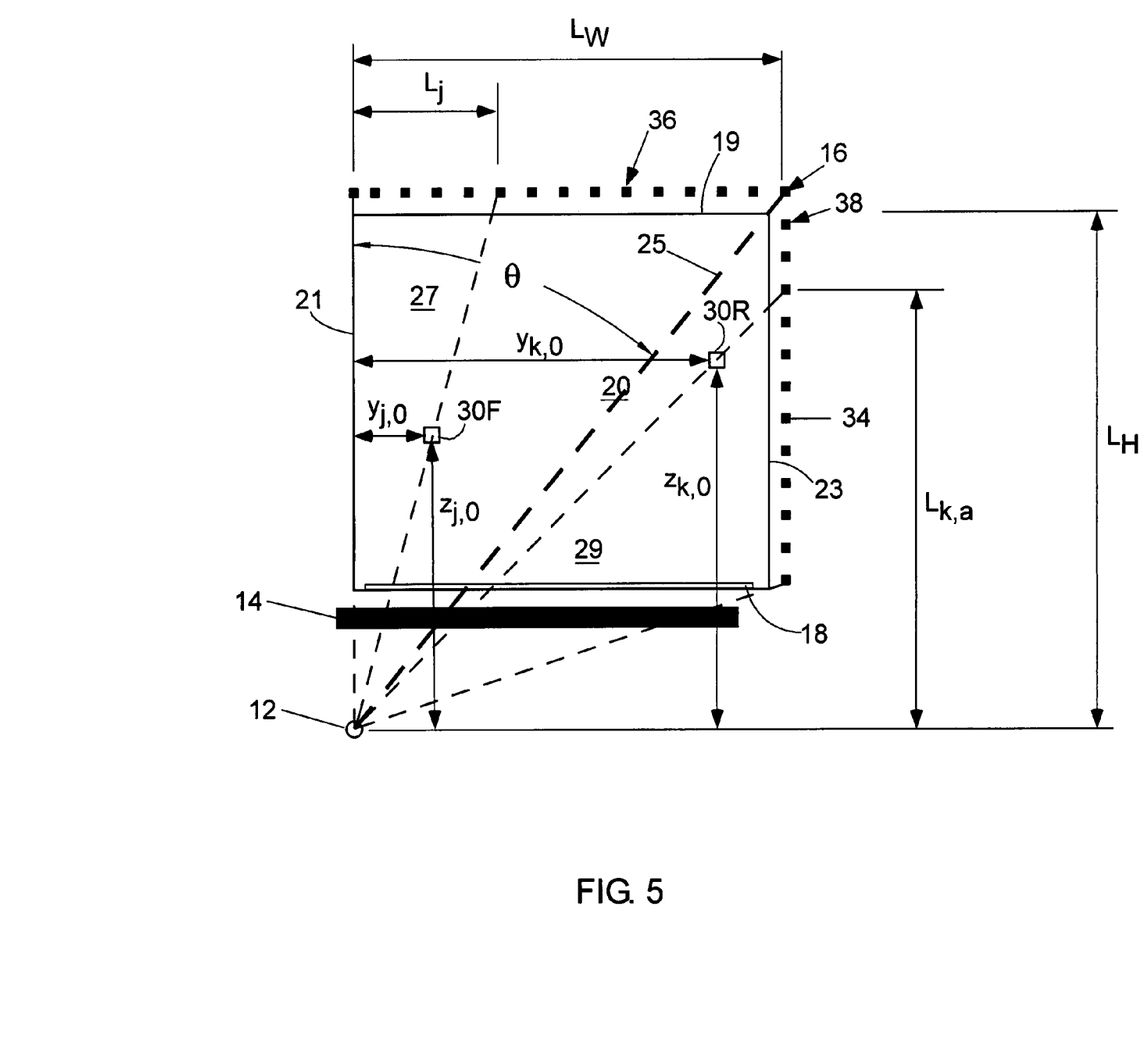
FIG. 5 is the end view of FIG. 3 showing the parameters of the operation of the single-source method of the present invention.

As can be seen in FIG. 5, every voxel falls in one of two regions 27, 29 of the imaging region 20, where the regions 27, 29 are defined by a dividing line 25 the runs between the x-ray source 12 and the opposite corner of the imaging region 20, that is, to the location of the upper most detector of the detector column 38. To focus a voxel 30F in the front region 27, the detectors 34 in the detector rows 36 are used, and to focus a voxel 30R in the rear region 29, detectors 34 in the detector columns 38 are used. The angle of the divider 25, denoted as $\theta$, is determined by the equation, $\theta = \arctan(L_W/L_H)$, where $L_W$ is the horizontal distance from the x-ray source 12 to any detector column 38 and $L_H$ is the vertical distance from the x-ray source 12 to any detector row 38.

In general, the method of the present invention operates in the following manner. The x-ray fan beams are emitted from a single location at different angles. The object to be imaged is propelled linearly through the fan beams such that each of the fan beams passes through the object. To focus a voxel in the object, the x-ray intensity of that portion of the fan beam passing through the voxel is read for each of the fan beams, resulting in a number of x-ray intensity readings for the voxel equaling the number of fan beams. The x-ray intensities are combined in accordance to standard laminography practice to generate an image for the voxel. The x-ray intensity readings and corresponding processing are performed for each voxel in the object and the resultant voxel images are used to produce an image of the entire object.

More particularly for the described embodiments, in order to focus a particular voxel, a detector 34 in each fan beam 24 that lines up with the voxel as it passes through the fan beam 24 is sampled and the x-ray intensities from those detectors are summed in accordance with the formula described below. This is done for every voxel 34 in the lateral direction (across the conveyor 18) within the central fan beam 24f. Since the chosen vertical column of voxels within the central fan beam 24f is not in any of the other fan beams, the desired focusing of a particular voxel is accomplished.

The chosen coordinate system has x in the direction of object motion 11, z in the vertical direction, and y perpendicular to the xz plane (laterally across the conveyor 18).

Figure 6:
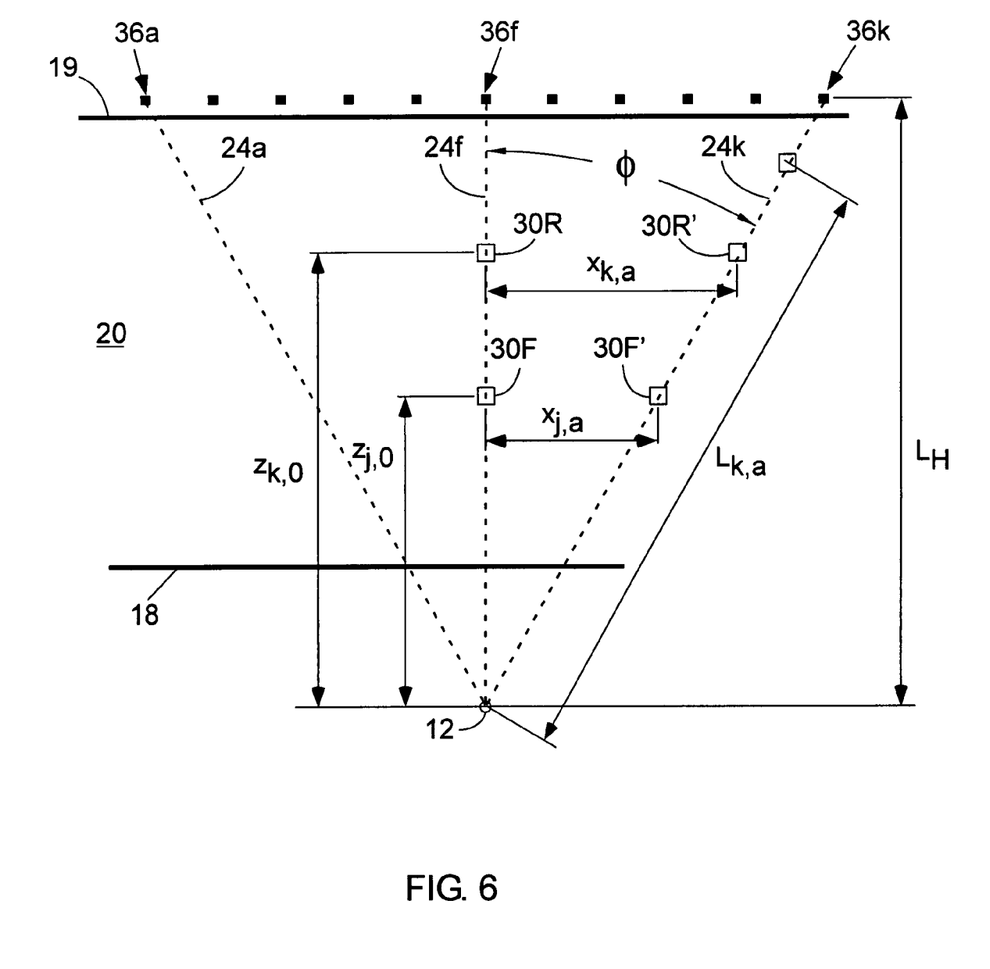
FIG. 6 is the side view of FIG. 1 showing the parameters of the operation of the single-source method of the present invention.

Referencing FIGS. 5 and 6, in order to focus a voxel, a detector in each fan beam that lines up with the voxel as it passes through the fan beam is sampled and the x-ray intensities from those detectors are summed. The relative distance, $x_{j,a}$, from the focused voxel 30F in the center fan beam 24f to the same voxel in another fan beam, shown as 30F' in FIG. 6, is given by the equation $x_{j,a} = z_{j,0} * \tan(\phi_a)$, where $z_{j,0}$ is the vertical distance from the x-ray source 12 to the voxel 30F. Assuming that the speed at which the object is moving is V, the time, $T_{j,a} - T_{j,0}$, that the voxel 30F passes through each of the fan beams 24 relative to the center fan beam 24f, that is, the relative time at which the detector should be sampled for the particular voxel 30F, is $T_{j,a} - T_{j,0} = x_{j,a}/V = (z_{j,0} * \tan(\phi_a))/V$. Note that the relative distance for detectors in fan beams 24a-e before the central fan beam 24f is a negative value, which means that the relative time is also negative, meaning that it is earlier than when the voxel passes through the central fan beam 24f. The location of the particular detector, $L_j$, in the detector row 36 to sample for the voxel 30F is determined by the equation $L_j = y_{j,0} * L_H / z_{j,0}$, where $y_{j,0}$ is the horizontal distance in the y direction of the voxel 30F from the x-ray source 12. Note that there is no relationship to the angle of the fan beam, $\phi_a$, because all of the detector rows 36 are identical, as described above.

The equivalent equation for the relative sampling time, $T_{k,a} - T_{k,0}$, for a voxel 30R to the rear of the dividing line 25 is $T_{k,a} - T_{k,0} = x_{k,a}/V = (z_{k,0} * \tan(\phi_a))/V$, where $z_k$ is the vertical distance from the x-ray source 12 to the voxel 30R. The location of the particular detector, $L_{k,a}$, in the detector column 38 to sample for the voxel 30R is determined by the equation $L_{k,a} = (L_W * z_{k,0})/(y_{k,0} * \cos(\phi_a))$, where $y_{k,0}$ is the horizontal distance in the y direction of the voxel 30R from the x-ray source 12. Note that $L_{k,a}$ is not a horizontal or vertical distance, but the diagonal distance along the detector column 38 extrapolated down to the x-ray source 12.

After applying these equations to every value of y and z, every voxel in the yz plane of the central fan beam 24f has been focused.

If the corresponding sample signal from the a'th fan beam and the j'th or k'th detector is $I_{j,a}$ or $I_{k,a}$, respectively, then the laminography blurred sum for each voxel in the vertical line in the central fan beam 24f when y=constant is $S_{j,Lam} = \Sigma I_{j,a}$ and $S_{k,Lam} = \Sigma I_{k,a}$, respectively, summed over all values of a.

The process is repeated for all of the additional values of $T_{j,0}$ and $T_{k,0}$ to focus additional vertical lines in the yz plane. Thus, a laminography image in the xz plane for a particular value of y is produced. This is a plane perpendicular to the horizontal.

To see a laminography image plane parallel to the conveyor 18, the line defined by z=constant in each xz plane for every value of y is viewed.

The process can be greatly improved by employing the second embodiment 9 of the present invention. The algorithm used in the single assemblage of the first embodiment 8 is applied to both assemblages 52, 54 of the second embodiment 9 in exactly the same fashion. The resultant "views" of the second assemblage 54 are different from the views produced by the first assemblage 52. The addition of the second assemblage 54 has the important feature that the additional assemblage allows views from a full 180° for all voxels in the object. Thus, computed tomography (CT) reconstruction algorithms can be used to produce CT imaging.

The present specification describes two apparatus embodiments where each x-ray detector assembly is comprised of a linear row of detectors and a linear column of detectors in an L-shaped configuration. The present invention also contemplates that other configurations of each detector assembly can be used. In general, any configuration of the detector assembly that can read the entirety of a fan beam passing through the imaging region can be used. One such example is an arc of detectors. The difference in implementing the method of the present invention for different detector assembly configurations lies in determining the location of the detector in the detector assembly to sample for each voxel, a simple matter of trigonometry.

Thus it has been shown and described a method and apparatus for producing laminography images using a fixed x-ray source which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

I claim:

1. An imaging system for taking an image of an object, said system comprising:
    (a) a mechanism adapted to propel said object linearly in a direction of motion through an imaging region, said region having a generally rectangular cross-section perpendicular to said direction of motion, said imaging region having a bottom, a top, a front, and a rear;
    (b) an x-ray source located below said bottom and aligned with or to the outside of said front, said x-ray source emitting an x-ray cone beam to said imaging region; and
    (c) a plurality of x-ray detector assemblies, each of said detector assemblies being comprised of a linear row of detectors above and substantially parallel to said top and perpendicular to said direction of motion, and a linear column of detectors outside of and substantially parallel to said rear and extending at an angle to said direction of motion, wherein each of said detector assemblies defines an x-ray fan beam within said x-ray cone beam.

2. The imaging system of claim 1 further comprising a plurality of collimators between said x-ray source and said imaging region, said collimators further defining said fan beams and reducing crosstalk between adjacent ones of said fan beams.

3. The imaging system of claim 1 wherein one of said fan beams is substantially perpendicular to said direction of motion.

4. The imaging system of claim 1 wherein said linear column angle is in the range of from −45° to +45°.

5. The imaging system of claim 1 wherein each of said detectors has a dimension in the direction of motion that is at least twice a dimension in the direction perpendicular to the direction of motion.

6. An imaging system for taking an image of an object, said system comprising:
    (a) a mechanism adapted to propel said object linearly in a direction of motion through an imaging region, said region having a generally rectangular cross-section perpendicular to said direction of motion, said imaging region having a bottom, a top, a front, and a rear;
    (b) a first x-ray assemblage comprised of a first x-ray source located below said bottom and aligned with or to the outside of said front, said first x-ray source emitting an x-ray cone beam to said imaging region; and a first plurality of x-ray detector assemblies, each of said first detector assemblies being comprised of a linear row of detectors above and parallel to said top and perpendicular to said direction of motion, and a linear column of detectors outside of and parallel to said rear and extending at an angle to said direction of motion, wherein each of said first detector assemblies defines an x-ray fan beam within said x-ray cone beam; and
    (c) a second x-ray assemblage comprised of a second x-ray source located outside said rear and aligned with or below said bottom, said second x-ray source emitting an x-ray cone beam to said imaging region; and a second plurality of x-ray detector assemblies, each of said second detector assemblies being comprised of a linear row of detectors outside and parallel to said front and perpendicular to said direction of motion, and a linear column of detectors above and parallel to said top and extending at an angle to said direction of motion, wherein each of said second detector assemblies defines an x-ray fan beam within said x-ray cone beam.

7. The imaging system of claim 6 further comprising a first plurality of collimators between said first x-ray source and said imaging region and a second plurality of collimators between said second x-ray source and said imaging region, said collimators further defining said fan beams and reducing crosstalk between adjacent ones of said fan beams.

8. The imaging system of claim 6 wherein one of said fan beams of said first x-ray assemblage and one of said fan beams of said second x-ray assemblage are substantially perpendicular to said direction of motion.

9. The imaging system of claim 6 wherein said linear column angle is in the range of from −45° to +45°.

10. The imaging system of claim 6 wherein each of said detectors has a dimension in the direction of motion that is at least twice a dimension in the direction perpendicular to the direction of motion.

11. A method of generating a three-dimensional digital tomographic image of an object composed of voxels, said method comprising the steps of:
    (a) emitting a plurality of x-ray fan beams, index a, from a single source location, each of said fan beams emitted at a different angle $\phi_a$ from said source location, one of said fan beams being a central fan beam, a=0, in a YZ plane wherein $\phi_0=0$;
    (b) receiving each of said fan beams at a corresponding line of detectors;
    (c) propelling said object linearly through said fan beams between said source location and said lines of detectors at velocity V in a direction X perpendicular to said YZ plane such that each of said fan beams passes through said object;
    (d) choosing a voxel at a location y,$z_0$ relative to said source location;
    (e) calculating the time $T_a$ when said voxel passes through each of said fan beams relative to said central fan beam as $T_a=(z_0*\tan(\phi_a))/V$;
    (f) reading an x-ray intensity at a detector in said line of detectors aligned with said source and said voxel at time $T_a$ for each of said plurality of fan beams;
    (g) combining said x-ray intensities to generate an image for said voxel;
    (h) repeating steps (d) through (g) for each voxel along the line z=constant and for all values of y of said object;
    (i) combining said voxel images to produce a line image for said line z=constant;
    (j) repeating steps (d) through (i) to produce line images for all values of z of said object;
    (k) combining said line images to produce a planar image in said YZ plane for a particular value of x of said object;

(l) repeating steps (d) through (k) to produce planar images for all values of x of said object; and (m) combining all of the said planar images to produce said three-dimensional digital tomographic image of said object.

12. The method of claim 11 further comprising performing steps (a) through (l) using a second single source location emitting fan beams that is 90° around said object from said single source location in a plane parallel to said YZ plane, and applying a standard computed tomography algorithm to said voxel images to produce views from a full 180 degrees for all of said voxels.

* * * * *